United States Patent
Dickhans et al.

(10) Patent No.: US 11,160,606 B2
(45) Date of Patent: Nov. 2, 2021

(54) SYSTEMS AND METHODS FOR LUNG TREATMENTS AND POST-TREATMENT SEALING OF LUNGS

(71) Applicant: COVIDIEN LP, Mansfield, MA (US)

(72) Inventors: William J. Dickhans, Longmont, CO (US); Kreg A. Howk, Auburn, MA (US)

(73) Assignee: COVIDIEN LP, Mansfield, MA (US)

(*) Notice: Subject to any disclaimer, the term of this patent is extended or adjusted under 35 U.S.C. 154(b) by 451 days.

(21) Appl. No.: 16/150,424

(22) Filed: Oct. 3, 2018

(65) Prior Publication Data
US 2019/0125435 A1 May 2, 2019

Related U.S. Application Data

(60) Provisional application No. 62/579,252, filed on Oct. 31, 2017.

(51) Int. Cl.
*A61B 18/14* (2006.01)
*A61B 18/18* (2006.01)
(Continued)

(52) U.S. Cl.
CPC ...... *A61B 18/1477* (2013.01); *A61B 17/3415* (2013.01); *A61B 18/1815* (2013.01);
(Continued)

(58) Field of Classification Search
CPC ............ A61B 18/1477; A61B 18/1815; A61B 2018/00541; A61B 2018/00577;
(Continued)

(56) References Cited

U.S. PATENT DOCUMENTS 6,770,070 B1 * 8/2004 Balbierz ............... A61B 10/04
600/566
6,964,639 B2 11/2005 Sela et al.
(Continued)

FOREIGN PATENT DOCUMENTS

WO 2015023834 A1 2/2015
WO 2016033066 A1 3/2016
(Continued)

OTHER PUBLICATIONS

Extended European Search Report issued in corresponding Appl. No. EP 18203508.9 dated Mar. 28, 2019 (7 pages).
(Continued)

*Primary Examiner* — Michael F Peffley
(74) *Attorney, Agent, or Firm* — Carter, DeLuca & Farrell LLP (57) ABSTRACT

A surgical system includes a stylus having a proximal end portion and distal end portion configured to penetrate lung tissue. The stylus may be movable between a first configuration and a second configuration within lung tissue. The surgical system may include a surgical instrument configured to treat lung tissue, a sealant configured to seal lung tissue, and an introducer configured for insertion into lung tissue. The introducer may have a proximal end portion and a distal end portion and may define a lumen therethrough configured to separately receive the stylus, the surgical instrument, and the sealant.

19 Claims, 9 Drawing Sheets

(51) Int. Cl.
  *A61B 34/10*    (2016.01)
  *A61B 17/34*    (2006.01)
  *A61B 18/00*    (2006.01)
  *A61B 8/12*     (2006.01)
  *A61B 17/00*    (2006.01)
  *A61B 90/00*    (2016.01)
  *A61B 34/20*    (2016.01)

(52) U.S. Cl.
  CPC ............... *A61B 34/10* (2016.02); *A61B 8/12* (2013.01); *A61B 2017/00809* (2013.01); *A61B 2018/0063* (2013.01); *A61B 2018/00541* (2013.01); *A61B 2018/00577* (2013.01); *A61B 2018/1425* (2013.01); *A61B 2018/183* (2013.01); *A61B 2018/1823* (2013.01); *A61B 2034/101* (2016.02); *A61B 2034/2051* (2016.02); *A61B 2090/378* (2016.02)

(58) Field of Classification Search
  CPC .... A61B 2018/0063; A61B 2018/1425; A61B 2018/1823; A61B 2018/183; A61B 17/3415; A61B 2017/00809; A61B 2034/101; A61B 2034/2051; A61B 2090/378; A61B 34/10
  See application file for complete search history.

(56) References Cited

U.S. PATENT DOCUMENTS

| | | | |
|---|---|---|---|
| 8,090,164 B2 | 1/2012 | Bullitt et al. | |
| 8,756,711 B2 | 6/2014 | Plodinec et al. | |
| 8,837,789 B2 | 9/2014 | Wei et al. | |
| 9,119,650 B2 | 9/2015 | Brannan et al. | |
| 9,247,992 B2 | 2/2016 | Ladtkow et al. | |
| 9,579,120 B2 | 2/2017 | Mauldin, Jr. et al. | |
| 2003/0083673 A1 | 5/2003 | Tierney et al. | |
| 2006/0025815 A1* | 2/2006 | McGurk ............ | A61B 17/00491 606/213 |
| 2007/0198008 A1 | 8/2007 | Hauck et al. | |
| 2009/0187164 A1 | 7/2009 | Rowe | |
| 2013/0006232 A1* | 1/2013 | Pellegrino ............ | A61B 18/12 606/33 |
| 2015/0073407 A1 | 3/2015 | Dickhans et al. | |
| 2016/0058507 A1 | 3/2016 | Dickhans | |
| 2016/0317224 A1* | 11/2016 | Girotto ............... | A61B 34/20 |
| 2016/0317229 A1 | 11/2016 | Girotto et al. | |
| 2017/0231695 A1* | 8/2017 | Dickhans ............ | A61B 34/20 606/33 |

FOREIGN PATENT DOCUMENTS

| | | |
|---|---|---|
| WO | 2016187456 A1 | 11/2016 |
| WO | 2017205326 A1 | 11/2017 |
| WO | 2018092136 A1 | 5/2018 |

OTHER PUBLICATIONS

Examination Report issued in corresponding European Appl. No. EP 18 203 508.9 dated Apr. 2, 2020 (4 pages).

Extended European Search Report issued in corresponding Appl. No. EP20187505.1 dated Oct. 9, 2020 (7 pages).

* cited by examiner

SYSTEMS AND METHODS FOR LUNG TREATMENTS AND POST-TREATMENT SEALING OF LUNGS

CROSS REFERENCE TO RELATED APPLICATION

The present application claims the benefit of and priority to U.S. Provisional Application Ser. No. 62/579,252, filed on Oct. 31, 2017 the entire contents of which are incorporated herein by reference.

BACKGROUND

1. Technical Field

The present disclosure relates to surgical systems, and more particularly, to systems and methods for treating a patient's lungs and post-treatment sealing of the lungs.

2. Discussion of Related Art

Treatment of certain diseases requires the destruction of malignant tissue growths, e.g., tumors. Electromagnetic (EM) radiation can be used to heat and destroy tumor cells. Treatment may involve inserting ablation antennas into or adjacent to tissues where cancerous tumors have been identified. Once the antennas are positioned, energy is passed through the antenna into surrounding tissue to treat, e.g., heat, ablate and/or coagulate tissue.

Ablation is a popular option for treating lung tissue, e.g., lung tumors. As with other surgical procedures, certain risks are involved with lung ablation. Piercing the lung wall with an ablation needle to access and treat a lung tumor may increase the risk of pneumothorax. Pneumothorax occurs when air leaks out of the lung into the space between the outside of the lung and the chest wall. The air trapped between the outside of the lung and the chest wall prevents the lung from fully expanding and may cause the lung to collapse.

SUMMARY

According to an aspect of the present disclosure, a surgical system is provided, including a stylus having a proximal end portion and distal end portion configured to penetrate lung tissue. The stylus may be movable between a first configuration and a second configuration within lung tissue. The surgical system may include a surgical instrument configured to treat lung tissue, a sealant configured to seal lung tissue, and an introducer configured for insertion into lung tissue. The introducer may have a proximal end portion and a distal end portion and may define a lumen therethrough configured to separately receive the stylus, the surgical instrument, and the sealant.

In embodiments, the distal end portion of the stylus may be configured to extend distally of the distal end portion of the introducer when a combination of the stylus and the introducer are inserted into lung tissue to create a track through lung tissue to a target. The surgical instrument may be configured for insertion into the lumen of the introducer and through the track in lung tissue to treat the target. The sealant may be configured to dispense through the lumen of the introducer to seal the track in lung tissue.

In some embodiments, the movement of the stylus within the introducer causes a corresponding movement of the introducer within lung tissue. The introducer may be configured to adopt and maintain the first and second configurations defined by the stylus to define the track through lung tissue.

In certain embodiments, the stylus is formed from a material selected from the group consisting of metal and ceramic.

In embodiments, the introducer is formed from a shape-memory material.

In some embodiments, the introducer is formed from a material selected from the group consisting of polyetheretherketone, fiberglass, and polymer.

In certain embodiments, the sealant is a material selected from the group consisting of a liquid, a gel, a foam, a paste, and aerosolized particles.

In embodiments, the sealant is formed from at least one of polyethylene glycol and human serum albumin and is configured to maintain the seal within lung tissue during expansion and contraction of lung tissue.

In some embodiments, the sealant is configured to create an airtight seal within the track, promote tissue growth, inhibit blood flow, resorb into the lung tissue, or activate immediately upon application to the lung tissue.

In certain embodiments, the surgical system includes an ultrasound imaging system, an ultrasound sensor, and a display. A combination of the ultrasound imaging system, the ultrasound sensor, and the display are configured to aid a user in positioning the stylus, the introducer, the surgical instrument, and the sealant within lung tissue.

In embodiments, the surgical system includes a biopsy tool configured for insertion into the lumen of the introducer and through the track in lung tissue to collect a sample of lung tissue.

In some embodiments, the surgical instrument is selected from the group consisting of a microwave ablation antenna, radiofrequency ablation antenna, and cryo-ablation antenna.

According to another aspect of the present disclosure, a method of performing a surgical procedure is provided, including inserting an introducer, and a stylus positioned through a lumen of the introducer, into a patient's lung to create a track to a target. The stylus may be removed from the lumen of the introducer while leaving the introducer in the created track. A surgical instrument may be inserted into the lumen of the introducer to access the target. The surgical instrument may be advanced through the lumen of the introducer until a radiating portion of the surgical instrument is proximate to the target such that the surgical instrument may radiate energy into the target. The surgical instrument may be removed from the introducer and a sealant may be dispensed through the lumen of the introducer for application to the patient's lung to seal the track.

In embodiments, an ultrasound imaging system, an ultrasound sensor, and a display may be provided to facilitate navigation of at least one of the introducer, the stylus, the surgical instrument, and the sealant through the patient's lung.

In some embodiments, any air leaks caused by the introducer and the stylus within the patient's lung are sealed with the sealant.

In certain embodiments, inserting a sealant through the lumen of the introducer for application to the patient's lung to seal the track includes withdrawing the introducer from the track while inserting the sealant.

In embodiments, lung tissue may be separated with at least one of the stylus and the introducer to access the target.

In some embodiments, the method includes inserting a biopsy tool into the lumen of the introducer and collecting a tissue sample with the biopsy tool.

According to another aspect of the present disclosure, a kit for use with a surgical system is provided, including a stylus configured to penetrate lung tissue, a surgical instrument configured to treat lung tissue, a sealant configured to seal lung tissue, and an introducer configured for insertion into lung tissue. The introducer may define a lumen therethrough configured to separately receive the stylus, the surgical instrument, and the sealant.

In embodiments, the surgical instrument is selected from the group consisting of a microwave ablation antenna, radiofrequency ablation antenna, and cryo-ablation antenna.

In some embodiments, the kit includes a biopsy tool configured to collect a sample of lung tissue.

BRIEF DESCRIPTION OF THE DRAWINGS

Objects and features of the present disclosure will become apparent to those of ordinary skill in the art when descriptions of various embodiments thereof are read with reference to the accompanying drawings, of which.

DETAILED DESCRIPTION

The present disclosure is directed to systems and methods for preventing pneumothorax during lung procedures, e.g., during lung ablation procedures. The combination of a stylus and an introducer are inserted into a patient's lung(s) to create a track to a target tissue site, e.g., a lung tumor. The stylus is then removed and a surgical instrument is inserted through the introducer to access the target, e.g., to treat the target. After accessing and/or treating the target, the surgical instrument is removed leaving only the introducer in the track. A sealant is then dispensed through the introducer to fill the track such that air does not escape from the lung after the surgical instrument is removed, e.g., after the ablation procedure is complete. As a result, pneumothorax following the procedure may be prevented, eliminating the need for follow-up procedures. These and other aspects and features of the present disclosure are detailed herein below.

Figure 1:
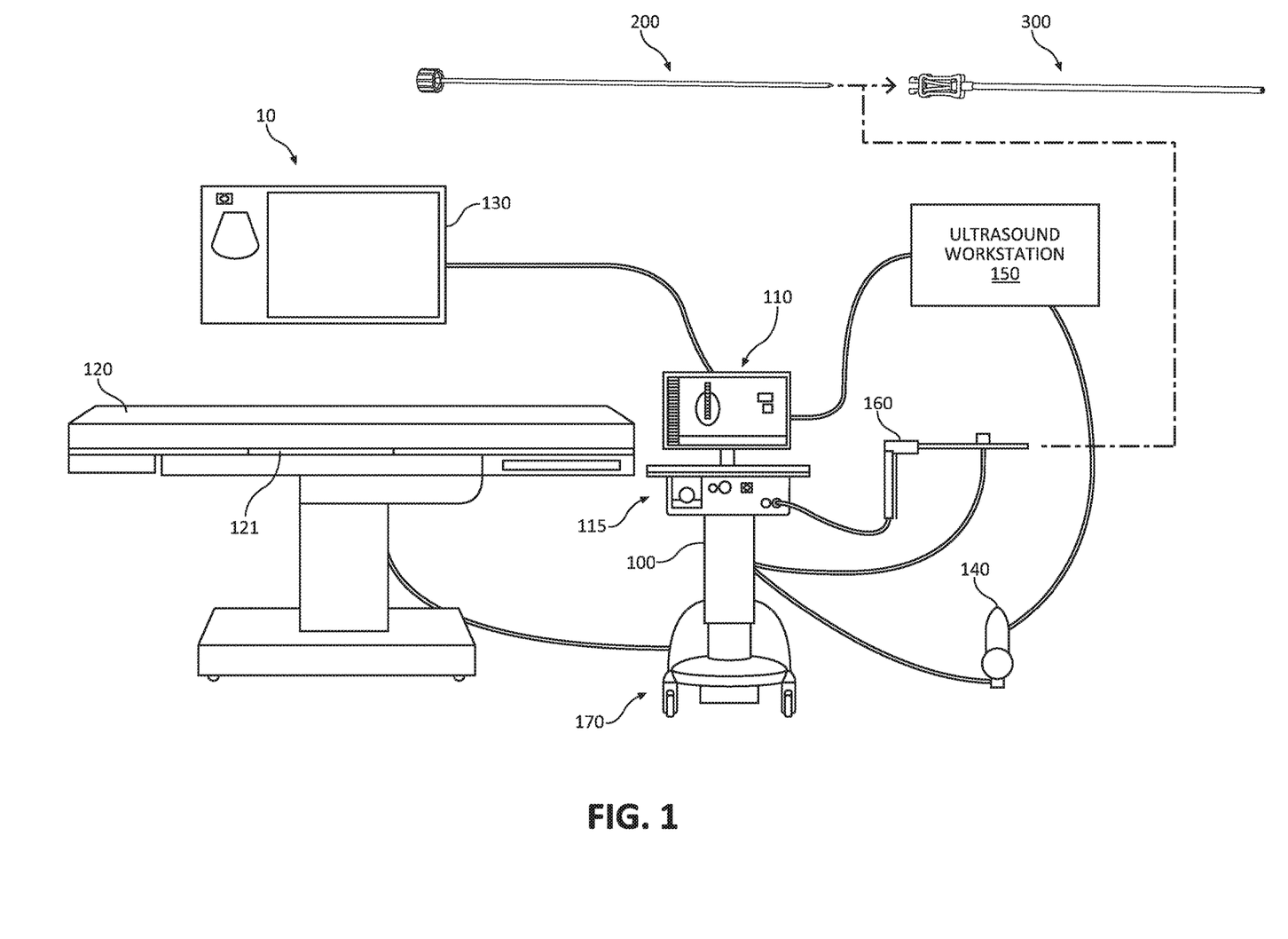
FIG. 1 is a side view of a lung treatment system provided in accordance with the present disclosure.

Referring now to FIG. 1, an exemplary lung treatment system 10 of the present disclosure is depicted. The lung treatment system 10 includes a computing device 100, a touch display computer 110, a generator 115, an operating table 120 including an electromagnetic (EM) field generator 121, a second display 130, an ultrasound imaging sensor 140, an ultrasound workstation 150, a surgical instrument 160, a base unit 170, a stylus 200, and an introducer 300.

Computing device 100 is configured for storing one or more treatment planning and electromagnetic tracking applications. Computing device 100 described herein may be, for example, a laptop computer, desktop computer, tablet computer, or other similar device.

Touch display computer 110 is configured to control generator 115, surgical instrument 160, and other accessories and peripheral devices relating to, or forming part of, lung treatment system 10. Touch display computer 110 is configured to present a user interface enabling a clinician to input instructions and settings for generator 115, display images, and/or messages relating to the performance of generator 115, the progress of a procedure, and issue alarms or alerts related to the same.

Operating table 120 may be any table suitable for use during a surgical procedure, which in certain embodiments includes, or is associated with, an electromagnetic (EM) field generator 121. EM field generator 121 is used to generate an EM field during a surgical procedure and forms part of an EM tracking system, which is used to track the positions of surgical instruments, e.g., surgical instrument 160 and ultrasound sensor 140, within the EM field around and within the body of a patient.

Second display 130, in association with computing device 100, may be used for displaying ultrasound imaging and providing visualization of tissue to be treated as well as navigation of surgical instrument 160. However, it is envisioned that touch display computer 110 and computing device 100 may also be used for ultrasound imaging and navigation purposes in addition to functions described above.

Ultrasound sensor 140, such as an ultrasound wand, may be used to image the patient's body during a procedure to visualize the location of surgical instrument 160 inside the patient's body. Ultrasound sensor 140 may have an EM tracking sensor embedded within or attached to the ultrasound wand, for example, a clip-on sensor or a sticker sensor. Ultrasound sensor 140 may be positioned in relation to surgical instrument 160 such that surgical instrument 160 is at an angle to the ultrasound image plane, thereby enabling the clinician to visualize the spatial relationship of surgical instrument 160 with the ultrasound image plane and with objects being imaged. Further, the EM tracking system may also track the location of ultrasound sensor 140. This spatial depiction of the ultrasound sensor 140 and the surgical instrument 160 is described in greater detail in U.S. Patent Publication No. 2016/0317229 entitled METHODS FOR MICROWAVE ABLATION PLANNING AND PROCEDURE, filed on Apr. 15, 2016 by Girotto, which is incorporated herein by reference. During surgery, one or more ultrasound sensors 140 may be placed on or inside the body of the patient. EM tracking system may then track the location of such ultrasound sensors 140 and surgical instrument 160 as they are moved relative to each other.

In addition to the EM tracking system, the surgical instruments, e.g., surgical instrument 160, may also be visualized by using ultrasound imaging work station 150. It is envisioned that ultrasound workstation 150 and its related components may be interchanged with real time fluoroscopy, MRI or CT imaging stations.

Surgical instrument 160 may be any type of surgical instrument, such as, e.g., a biopsy tool, microwave ablation antenna, radiofrequency ablation antenna, cryo-ablation antenna, etc. For example, surgical instrument 160 may be used to ablate tissue, e.g., a lesion or tumor (hereinafter referred to as a "target"), by using energy to heat tissue in order to denature or kill cancerous cells. Examples of ablation antennas and systems are described in U.S. Patent Publication No. 2016/0058507 entitled MICROWAVE ABLATION SYSTEM, filed on Aug. 18, 2015 by Dickhans, International Application No. PCT/US15/46729 entitled MICROWAVE ABLATION SYSTEM, filed on Aug. 25, 2015 by Dickhans, U.S. Patent Publication No. 2014/0046315 entitled MICROWAVE ABLATION CATHETER AND METHOD OF UTILIZING THE SAME, filed on Mar. 15, 2013 by Ladtkow et al., U.S. Patent Publication No. 2014/0276739 entitled MICROWAVE ENERGY-DELIVERY DEVICE AND SYSTEM, filed on Mar. 15, 2013 by Brannan et al., the entire contents of each of which are incorporated herein by reference and may be used in conjunction with the aspects and features of the present disclosure.

Base unit 170 may be a cart, stand, console, and/or station configured to support the computing device 100, the generator 115, and the touch display computer 110.

Figure 2:
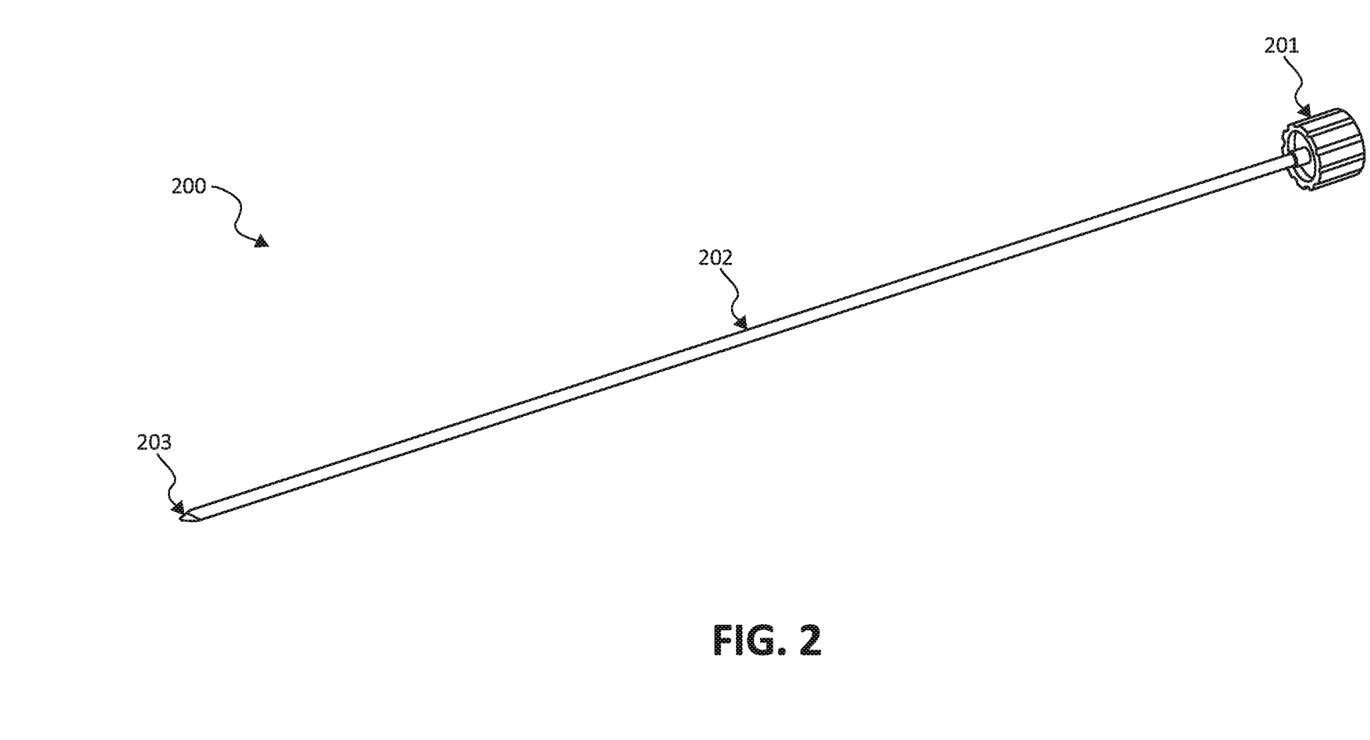
FIG. 2 is a perspective view of a stylus configured for use with the lung treatment system of FIG. 1.

With reference to FIG. 2, stylus 200 includes a cap 201, a shaft 202, and a tip 203 defined at a distal end portion thereof. Stylus 200 is configured for insertion into introducer 300, as will be described in greater detail below. Stylus 200 may be formed of a metallic or non-metallic (e.g., ceramic MRI compatible) rigid or semi-rigid material having the ability to traverse tissue. In embodiments, stylus 200 may be formed of a material that is visible in real time ultrasound, CT, MRI, or other imaging systems. Cap 201 of stylus 200 may have a lumen (not shown) for ejectment of fluids (e.g., blood), or so that other devices (e.g., guide wires) may be inserted into the lumen through shaft 202 of stylus 200. Cap 201 may also have a lock fitting for attachment to other devices, such as fitting 301 of introducer 300, surgical instrument 160, guide wires, extending working channels, or the like. Shaft 202 of stylus 200 may be any length (e.g., 10 cm, 15 cm, 20 cm, etc.) and may have a substantially straight or, alternatively, a curved profile. Stylus 200 may also be articulable and/or steerable between a straight configuration and a curved configuration to accommodate a specific surgical procedure, a specific luminal structure, specific target tissue, a clinician's preference, etc. For example, a user may manipulate shaft 202 of stylus 200 to adopt a curved profile such that stylus 200 may traverse critical tissue structures or narrow pathways to reach a target site. Tip 203 of stylus 200 may be a sharp edge for penetrating skin, such as a single bevel, dual bevel, or the like.

Figure 3:
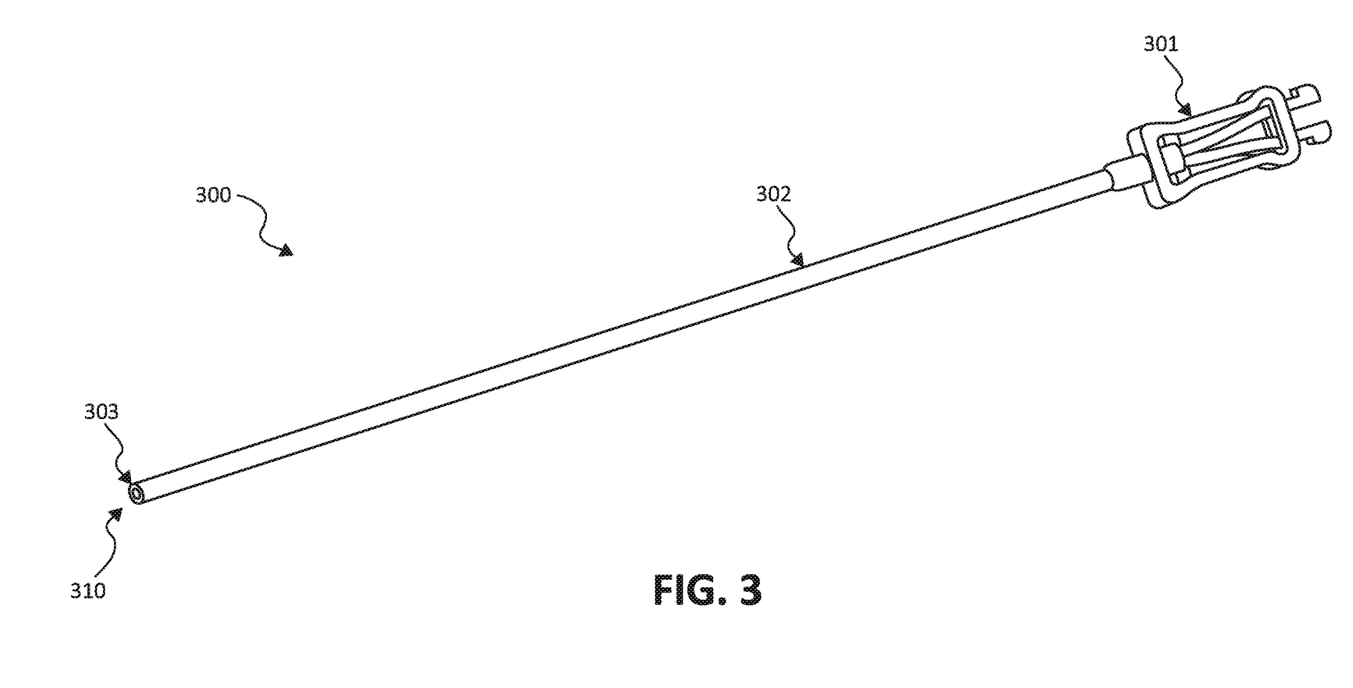
FIG. 3 is a perspective view of an introducer configured for use with the lung treatment system of FIG. 1.

With reference to FIG. 3, introducer 300 is configured to receive stylus 200 and/or surgical instrument 160, as will be described in greater detail below. Introducer 300 defines a lumen 310 and includes a fitting 301, a shaft 302, and a distal end portion or free end 303. Introducer 300 may be formed from Polyether ether ketone (PEEK), fiberglass, or any other plastic, polymer, or the like. In some embodiments, introducer 300 may be formed of a material visible in real time ultrasound, CT, or MRI imaging. Depth markers (not shown) may be placed on shaft 302 of stylus 300 for indicating distance (e.g., in real time ultrasound, CT, or MRI imaging). Introducer 300 is formed from a non-conductive (e.g., non-metallic) material allowing surgical instrument 160 to radiate through introducer 300. Introducer 300 may be rigid, semi-rigid, or flexible and may be formed of a shape-memory material, such that it can adopt and maintain the profile (e.g., curved) of steerable stylus 200. Fitting 301 of introducer 300 may have a lumen (not shown) for connection and/or insertion of other devices (e.g., guide wires, extended working channels, surgical instrument 160, stylus 200, etc.). Fitting 301 may include or be adapted for use with a luer lock/adapter such that fitting 301 can be connected to a needle, syringe, or other fluid injecting or dispensing device for insertion and/or injection of fluids through lumen 310 of introducer 300 into lung tissue. Shaft 302 of introducer 300 may be fabricated of any length suitable to reach a target site. Likewise, shaft 302 of introducer 300 may have any suitable outer diameter for passage into and through tissues, vessels, or other luminal networks, or any suitable inner diameter, e.g., lumen 310, for the insertion of other devices (e.g., surgical instrument 160, stylus 200, etc.) through lumen 310.

Figure 4:
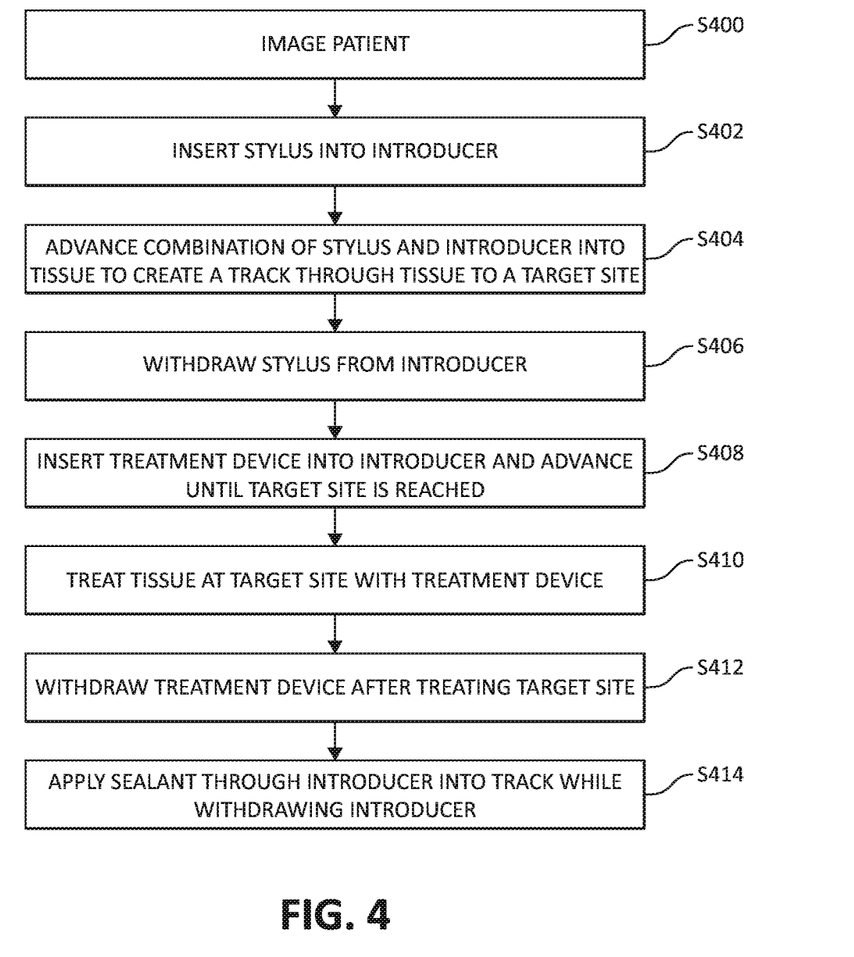
FIG. 4 is a flow chart depicting a method of performing a lung procedure.

Referring now to FIG. 4, a flowchart of a method for performing a lung procedure is depicted. The flowchart of FIG. 4 is not intended to have any limiting effect or to imply any order of steps. To this end, the methods illustrated and described herein may include some or all of the steps described and may be implemented in any order not specifically described. The flowchart in FIG. 4 will be referenced herein below, where applicable, to describe the steps of performing a lung ablation procedure.

Figure 5:
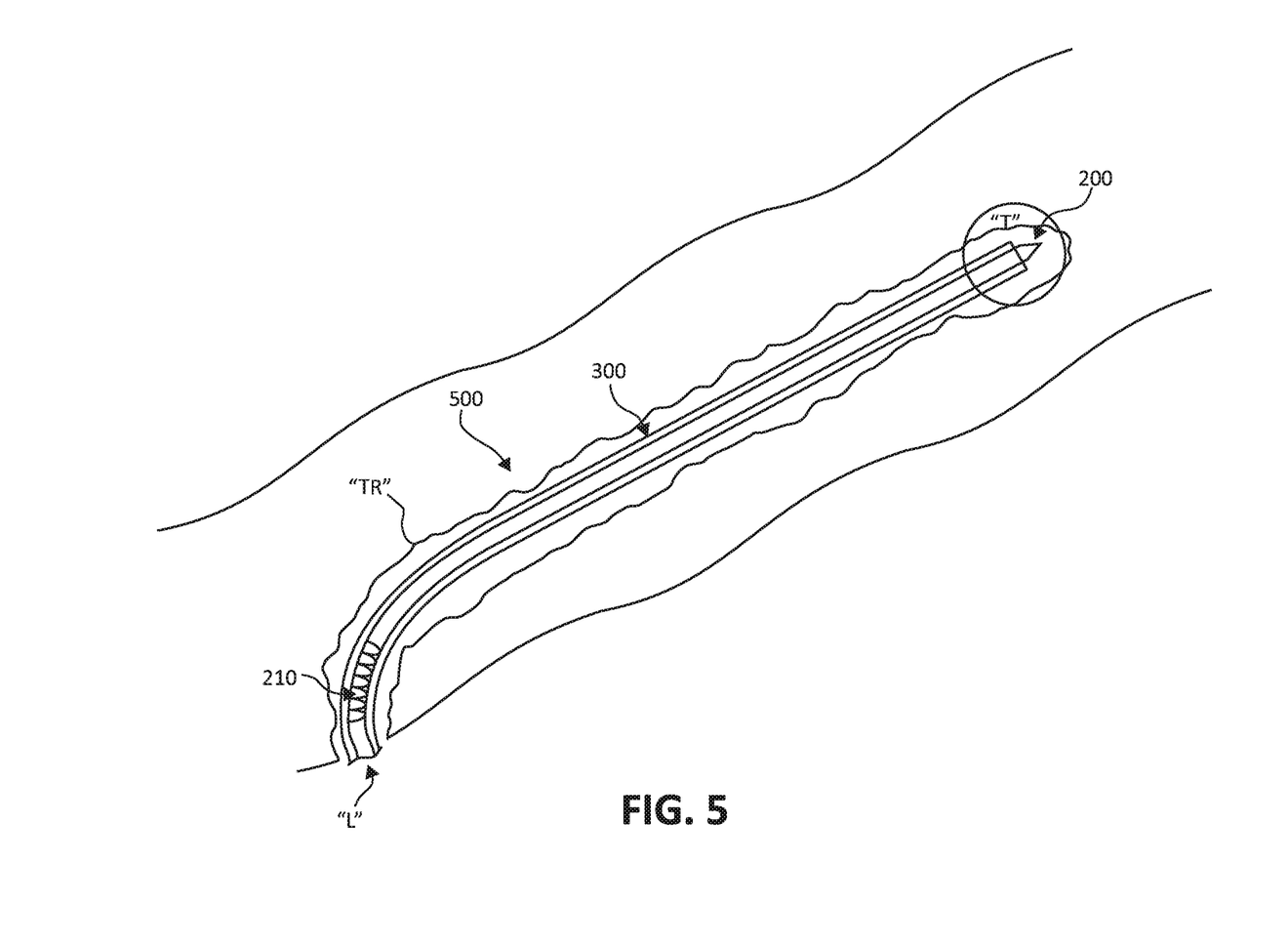
FIG. 5 is a schematic diagram of a cross-sectional view of an access assembly placed into tissue.

Referring now to FIG. 5, an access assembly 500 is depicted, which includes stylus 200 and introducer 300, as shown inside a body cavity, e.g., a lung. During use, in step S400, stylus 200 is inserted into introducer 300 and aligned coaxially therewith. In step S402, the combination of the stylus 200 and introducer 300 are inserted together as access assembly 500. Tip 203 of stylus 200 protrudes from free end 303 of introducer 300 for puncturing skin and advancing access assembly 500 to a desired target. In step S404, stylus 203 of access assembly 500 has punctured the surface of a patient's lung at an entrance site "L" and created a track "TR" through the lung into a target "T." Stylus 200 may be manipulated, articulated, and/or steered to avoid critical tissue structures and to reach the target "T." For example, as shown in FIG. 5, stylus 200 may include an articulation joint 210, which may be articulated by using a dial or other suitable actuating device (not shown) that is separate from or integral with cap 201 of stylus 200. Advantageously, tissue separation is done by access assembly 500 and not surgical instrument 160. As such, access assembly 500 assists in eliminating stresses applied to the surgical instrument 160 during a procedure.

With continued reference to FIG. 5, introducer 300 dynamically adopts and maintains the path of stylus 200 even after the formed stylus 200 is removed. Although stylus 200 and introducer 300 are shown as having a single curved configuration, it should be appreciated that stylus 200 and introducer 300 of access assembly 500 may adopt a trajectory having any configuration (e.g., straight, a plurality of curves, etc.) suitable for reaching challenging targets. After the desired target "T" has been reached, in step S406, stylus 200 may be withdrawn from introducer 300, with introducer 300 maintaining the trajectory that formed stylus 200 had prior to its removal from introducer 300. After removal of stylus 200, introducer 300 may be maintained in place, e.g., in track "TR," by the body's natural pressures such that removal of the stylus 200 leaves behind the flexible introducer 300, which can be, e.g., compressed and held in place by the tissue in which it is inserted, e.g., lung tissue. As such, introducer 300 maintains access to the target "T" and, in step S408, surgical instrument 160 may be inserted into introducer 300 (not shown) to, in step S410, perform ablation of target "T" through introducer 300.

Figure 6:
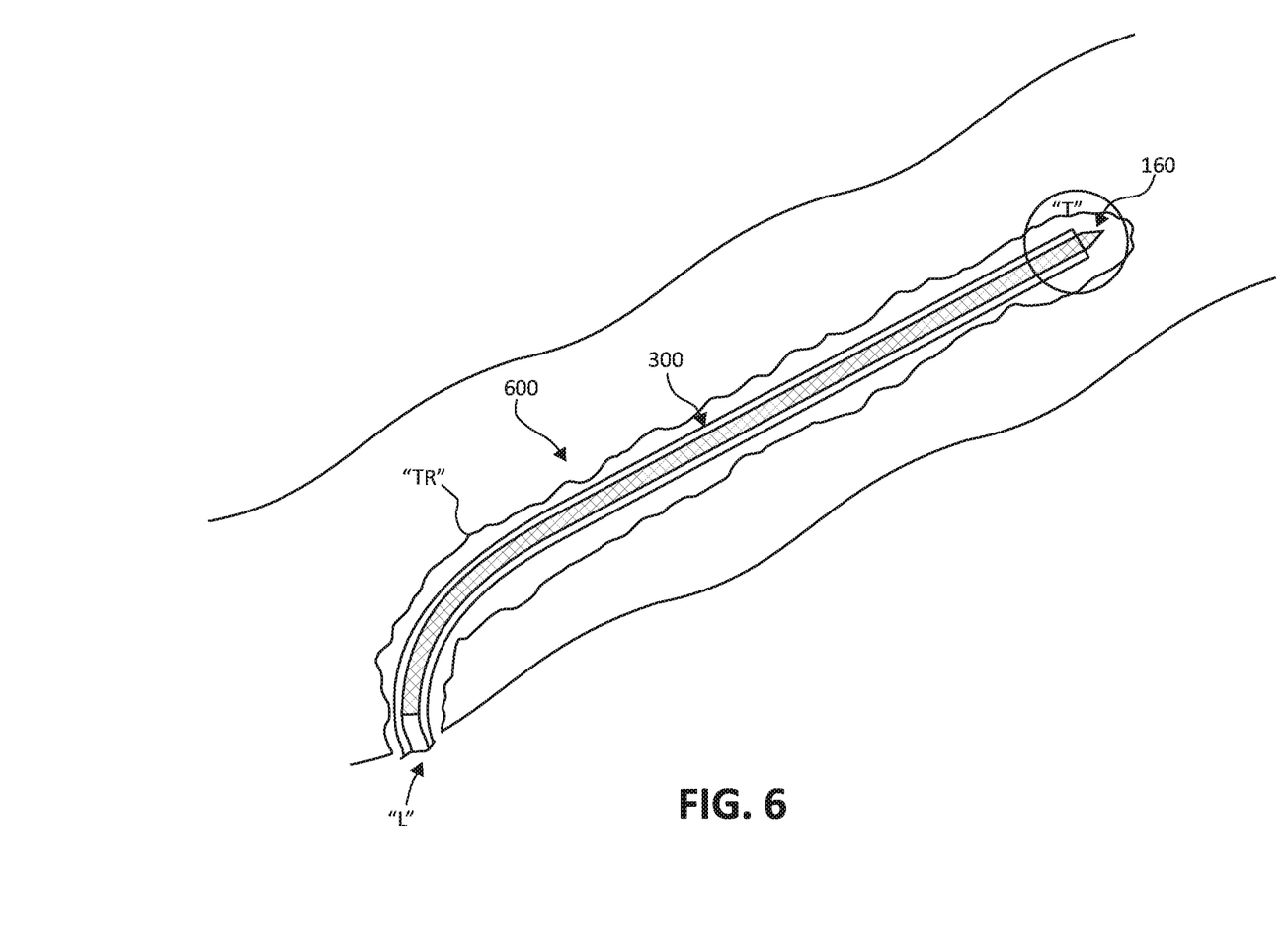
FIG. 6 is a cross-sectional view of a treatment assembly placed into tissue.

Referring now to FIG. 6, a treatment assembly 600 is shown, including surgical instrument 160 and introducer 300. In steps S408 and S110, surgical instrument 160 is inserted and advanced into introducer 300 for treatment of lung tissue, e.g., target "T," or to collect a tissue sample to perform a biopsy. In step S412, after ablation of target "T" is completed, surgical instrument 160 may be withdrawn from introducer 300.

Figure 7:
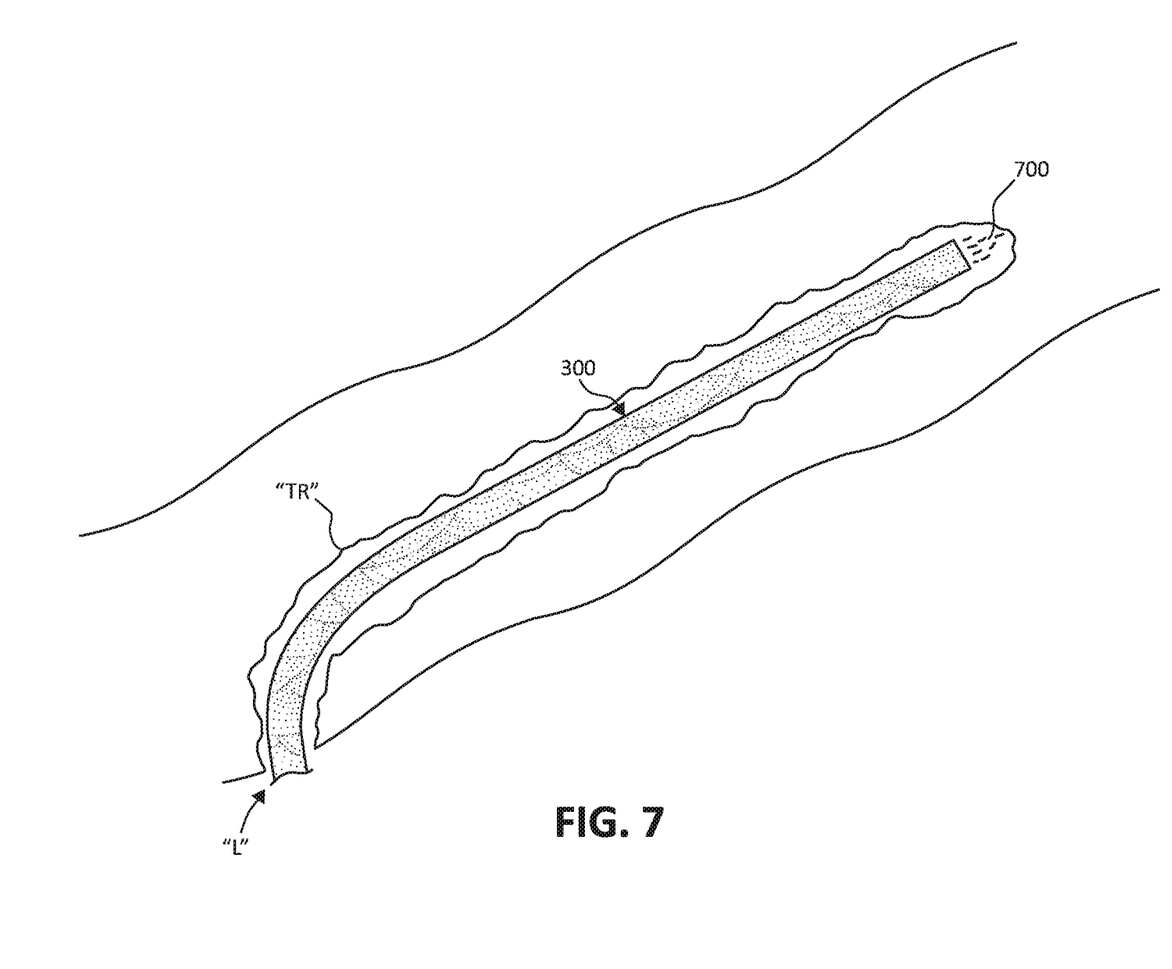
FIG. 7 is a cross-sectional view of the introducer with a sealant disposed in a lumen thereof and placed into lung tissue.

Referring now to FIG. 7, in step S414, a sealant 700 is applied through lumen 310 of introducer 300. Sealant 700 may be used to seal air leaks in the lung(s) following ablation of target "T." As described above, the surface of the lung is punctured at site "L," e.g., in order to create a track "TR" to access and treat target "T" (FIG. 5). Puncturing the lung during a lung ablation procedure may increase the risk of pneumothorax. Pneumothorax occurs when air leaks from the punctured lung into the pleural cavity between the surface of the lung and the chest wall. The leaked air produces excess pressure on the lung, preventing the lung from fully expanding and causing the lung to collapse.

In order to reduce or eliminate the risk of pneumothorax, sealant 700 is applied to a tissue site, e.g. entrance site "L" and track "TR" (FIGS. 5 and 6) within the lungs to seal any lung air leaks that may have resulted from the insertion of a surgical instrument (e.g., a microwave ablation antenna, stylus, etc.) through lung tissue during the procedure. Sealant 700 may be a liquid, a gel, a hydrogel, a foam, a paste, aerosolized particles, or the like, formed specifically for application to lung tissue. For example, sealant 700 may be formed to adhere to lung tissue, create an airtight seal, promote tissue growth, inhibit blood flow, and resorb into lung tissue. Sealant 700 may also be strong enough to withstand re-expansion of the lung immediately upon application, while being elastic enough to allow the lung to expand and contract naturally during respiration. In some embodiments, sealant 700 may be formed from polyethylene glycol (PEG) to enhance elasticity and human serum albumin (HAS) to enhance adhesive strength. Sealant 700 may be fast acting, e.g., activated immediately after coming into contact with lung tissue and body liquids upon dispensation. Following the surgical procedure, sealant 700 may be resorbed into the body such that it does not have to be surgically removed in a follow up procedure. Sealant 700 will be biocompatible per current ISO 10993 standards.

Sealant 700 may be inserted directly into lumen 310 of introducer 300. Additionally or alternatively, a peripheral device (not shown), such as a tube, plunger, applicator, syringe, or the like, may be coupled to fitting 301 (FIG. 3) of introducer 300 to inject or insert sealant 700 into lumen 310 of introducer 300 such that sealant 700 may be applied to entrance site "L" and track "TR" (FIGS. 5, 6 and 7). In use, sealant 700 may be dispensed through lumen 310 from free end 303 of introducer 300 into lung tissue to fill track "TR" and to plug the hole at entrance site "L" at the surface of the lung. In embodiments, sealant 700 may be dispensed from free end 303 (FIG. 3) of introducer 300 in the process of withdrawing introducer 300 from the patient's lung such that sealant 700 may be applied at several locations within track "TR" to ensure adequate delivery throughout track "TR." After application of sealant 700, introducer 300 may be withdrawn from the patient's lung to complete the surgical procedure. Thus, advantageously, follow-up procedures for removing air between the lung and chest wall, e.g., needle aspiration, chest tubes drainage, and the like, are not necessary as pneumothorax is prevented during the ablation procedure with application of sealant 700 to lung tissue.

Figure 8:
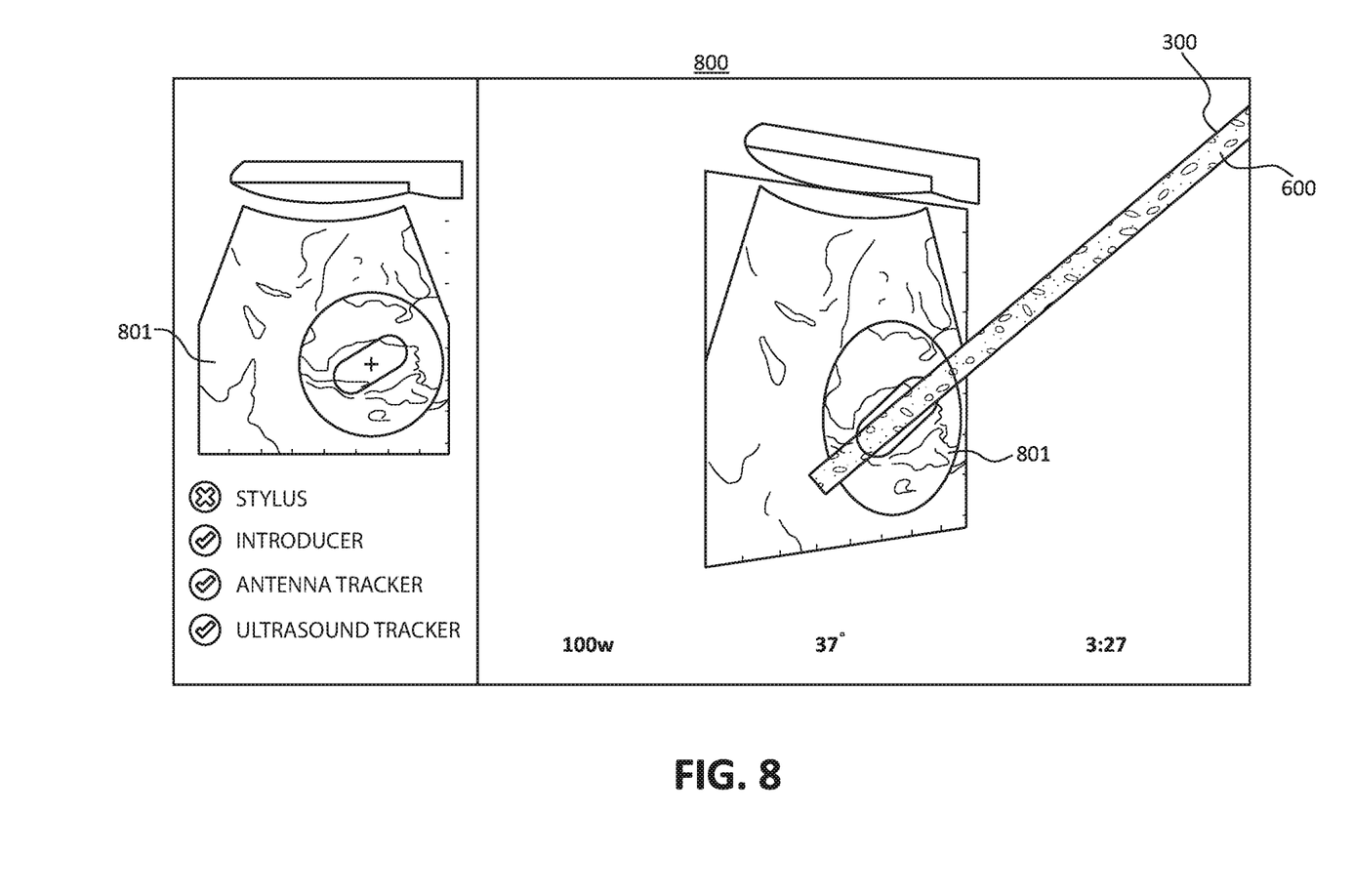
FIG. 8 is an illustration of a user interface presenting a view during a surgical procedure.

Referring now to FIG. 8, an example screen 800 is shown, which may be displayed on touch display computer 110 or display 130 during a surgical procedure, e.g., a microwave ablation procedure. Screen 800 includes a view 801 of the live 2D ultrasound (or real time CT, MRI, fluoroscopy, etc.) images captured during the procedure. Screen 800 may aid a user in the positioning of surgical instrument 160, stylus 200, introducer 300, access assembly 500, treatment assembly 600, sealant 700, or any other devices used in the procedure. Ultrasound sensor 140 may be positioned in relation to the aforementioned devices such that they are at an angle to the ultrasound image plane, thereby enabling the clinician to visualize their spatial relationship with the ultrasound image plane and with objects being imaged. Following ablation of target "T," as well as application of sealant 700 to track "TR" and entrance site "L," screen 800 may be used to visualize and confirm that any holes or punctures within the patient's lungs have been closed and that air is not leaking from the patient's lung into, e.g., the pleural cavity as a result of the ablation procedure. As can be appreciated, other imaging techniques such as fluoroscopy, CT, and MRI may be used with and/or separately from ultrasound workstation 150 to, e.g., visualize and confirm placement of stylus 200, introducer 300, surgical instrument 160, access assembly 500, treatment assembly 600, and/or sealant 700 within lung tissue.

Figure 9:
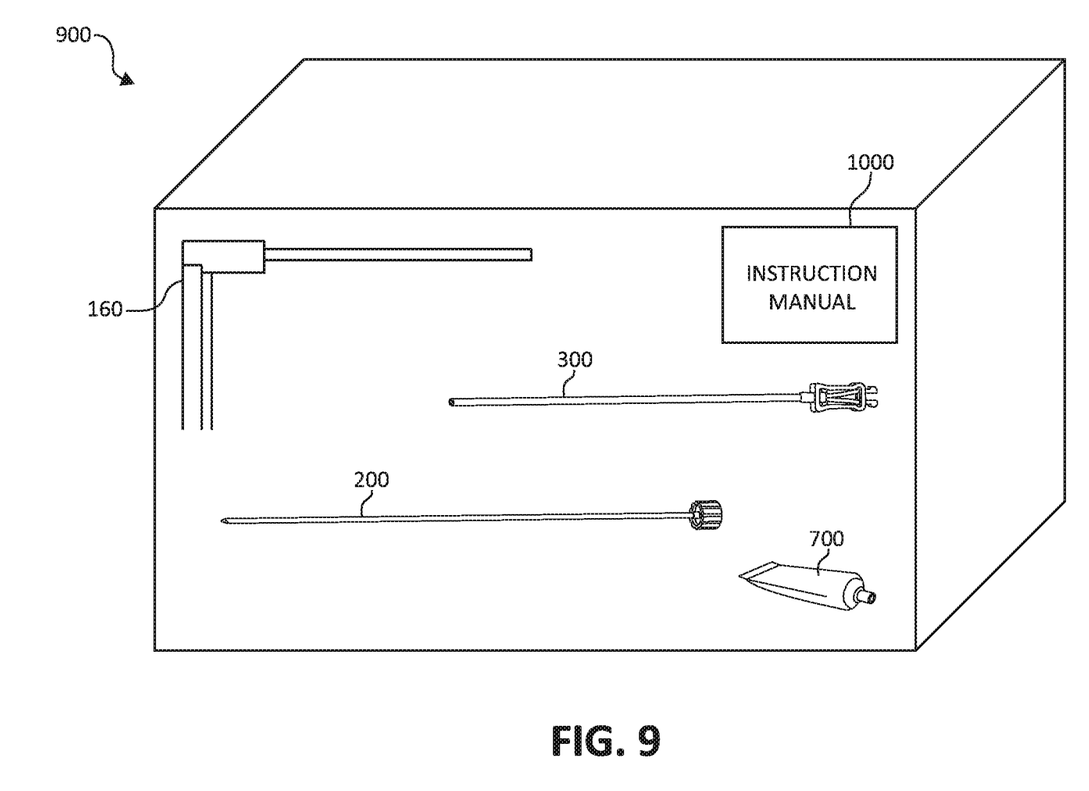
FIG. 9 is a schematic illustration of a surgical instrument kit.

With reference to FIG. 9, a surgical instrument kit is shown and generally designated as 900. Kit 900 includes surgical instrument 160, stylus 200, introducer 300, sealant 700, and an instruction manual 1000 for operating the aforementioned devices and performing, e.g., a lung treatment procedure. It is contemplated and within the scope of the present disclosure that the kit 900 may include one or more surgical instruments 160, stylus 200, introducers 300, and/or sealants 700.

The devices, systems, and methods described herein are applicable to any type of surgical procedure and are not limited to lung procedures. Although embodiments have been described in detail with reference to the accompanying drawings for the purpose of illustration and description, it is to be understood that the inventive processes and apparatus are not to be construed as limited thereby and that they may be used with other tissue structures. It will be apparent to those of ordinary skill in the art that various modifications to the foregoing embodiments may be made without departing from the scope of the disclosure.

What is claimed is:

1. A surgical system, comprising:
 a stylus having a proximal end portion, and a distal end portion configured to penetrate lung tissue, the stylus movable between a first configuration and a second configuration within lung tissue;
 a surgical instrument configured to treat lung tissue;
 a sealant configured to seal lung tissue;
 an introducer configured for insertion into lung tissue and having a proximal end portion and a distal end portion, the introducer defining a lumen therethrough configured to separately receive the stylus, the surgical instrument, and the sealant, wherein during use for a lung procedure:
  the distal end portion of the stylus is configured to extend distally of the distal end portion of the introducer such that the stylus punctures an outer surface of a patient's lung to create an entrance site;
  a combination of the stylus and the introducer is configured to advance through the entrance site to create a track from the entrance site through lung tissue to a target;
  the surgical instrument is configured, after the stylus is removed from the lumen, to be inserted into the lumen of the introducer and through the track to treat the target; and the sealant is configured, after the surgical instrument is removed from the lumen, to dispense through the lumen of the introducer while the introducer is moving through the track away from the target and through the entrance site for removal of the introducer from the patient's lung to seal the track and the entrance site.

2. The surgical system of claim 1, wherein movement of the stylus within the introducer causes a corresponding movement of the introducer within lung tissue, the introducer configured to adopt and maintain the first and second configurations defined by the stylus to define the track through lung tissue.

3. The surgical system of claim 1, wherein the stylus is formed from a material selected from the group consisting of metal and ceramic.

4. The surgical system of claim 1, wherein the introducer is formed from a shape-memory material.

5. The surgical system of claim 1, wherein the introducer is formed from a material selected from the group consisting of polyetheretherketone, fiberglass, and polymer.

6. The surgical system of claim 1, wherein the sealant is a material selected from the group consisting of a liquid, a gel, a foam, a paste, and aerosolized particles.

7. The surgical system of claim 1, wherein the sealant is formed from at least one of polyethylene glycol and human serum albumin, the sealant configured to maintain the seal within lung tissue during expansion and contraction of lung tissue.

8. The surgical system of claim 1, wherein the sealant is configured to create an airtight seal within the track, promote tissue growth, inhibit blood flow, resorb into the lung tissue, or activate immediately upon application to the lung tissue.

9. The surgical system of claim 1, further comprising:
an ultrasound imaging system, an ultrasound sensor, and a display; and
wherein a combination of the ultrasound imaging system, the ultrasound sensor, and the display are configured to aid a user in positioning the stylus, the introducer, the surgical instrument, and the sealant within lung tissue.

10. The surgical system of claim 1, further comprising a biopsy tool configured for insertion into the lumen of the introducer and through the track in lung tissue to collect a sample of lung tissue.

11. The surgical system of claim 1, wherein the surgical instrument is selected from the group consisting of a microwave ablation antenna, radiofrequency ablation antenna, and cryo-ablation antenna.

12. A method of performing a surgical procedure, comprising:
inserting an introducer, and a stylus positioned through a lumen of the introducer, through an outer surface of a patient's lung to create an entrance site and through lung tissue to create a track extending from the entrance site to a target;
removing the stylus from the lumen of the introducer while leaving the introducer in the created track;
inserting a surgical instrument into the lumen of the introducer to access the target;
advancing the surgical instrument through the lumen of the introducer until a radiating portion of the surgical instrument is proximate to the target;
radiating energy from the surgical instrument into the target;
removing the surgical instrument from the introducer;
moving the introducer through the track away from the target and through the entrance site to remove the introducer from the patient's lung; and
dispensing a sealant through the lumen of the introducer while the introducer is moving through the track away from the target and through the entrance site for removal of the introducer from the patient's lung to seal the track and the entrance site.

13. The method of claim 12, further comprising:
providing an ultrasound imaging system, an ultrasound sensor, and a display to facilitate navigation of at least one of the introducer, the stylus, the surgical instrument, and the sealant through the patient's lung.

14. The method of claim 12, further comprising sealing, with the sealant, any air leaks caused by the introducer and the stylus within the patient's lung.

15. The method of claim 12, further comprising separating lung tissue with at least one of the stylus and the introducer to access the target.

16. The method of claim 12, further comprising:
inserting a biopsy tool into the lumen of the introducer; and
collecting a sample of tissue with the biopsy tool.

17. A kit for use with a surgical system, comprising:
a stylus configured to penetrate lung tissue;
a surgical instrument configured to treat lung tissue;
a sealant configured to seal lung tissue; and
an introducer configured for insertion into lung tissue, the introducer defining a lumen therethrough configured to separately receive the stylus, the surgical instrument, and the sealant, wherein during use for a lung procedure:
a distal end portion of the stylus is configured to extend distally of a distal end of the introducer such that the stylus punctures an outer surface of a patient's lung to create an entrance site;
a combination of the stylus and the introducer is configured to advance through the entrance site to create a track from the entrance site through lung tissue to a target;
the surgical instrument is configured, after the stylus is removed from the lumen, to be inserted into the lumen of the introducer and through the track to treat the target; and
the sealant is configured, after the surgical instrument is removed from the lumen, to dispense from the distal end of the introducer while the introducer is moving through the track away from the target and through the entrance site for removal of the introducer from the patient's lung to seal the track and the entrance site.

18. The kit of claim 17, wherein the surgical instrument is selected from the group consisting of a microwave ablation antenna, radiofrequency ablation antenna, and cryo-ablation antenna.

19. The kit of claim 17, further comprising a biopsy tool configured to collect a sample of the lung tissue.

* * * * *